United States Patent
Atkins (10) Patent No.: US 12,048,455 B2
(45) Date of Patent: Jul. 30, 2024

(54) SURGICAL INSTRUMENTS

(71) Applicant: AT ORTHO LIMITED, Bristol (GB)

(72) Inventor: Roger Michael Atkins, Bristol (GB)

(73) Assignee: AT ORTHO LIMITED, Bristol (GB)

( * ) Notice: Subject to any disclaimer, the term of this patent is extended or adjusted under 35 U.S.C. 154(b) by 657 days.

(21) Appl. No.: 17/255,986

(22) PCT Filed: Jun. 25, 2019

(86) PCT No.: PCT/EP2019/066899
§ 371 (c)(1),
(2) Date: Dec. 23, 2020

(87) PCT Pub. No.: WO2020/002365
PCT Pub. Date: Jan. 2, 2020

(65) Prior Publication Data
US 2021/0220004 A1    Jul. 22, 2021

(30) Foreign Application Priority Data

Jun. 25, 2018   (GB) ..................................... 1810403
Mar. 11, 2019   (GB) ..................................... 1903277

(51) Int. Cl.
*A61B 17/3213*   (2006.01)
*A61B 17/32*     (2006.01)
(Continued)

(52) U.S. Cl.
CPC .... *A61B 17/3213* (2013.01); *A61B 17/32093* (2013.01); *A61B 17/1717* (2013.01); *A61B 2017/320052* (2013.01)

(58) Field of Classification Search
CPC ...... A61B 17/3209–3213; A61B 17/17; A61B 17/1717
(Continued)

(56) References Cited

U.S. PATENT DOCUMENTS 3,998,229 A    12/1976  Barton
5,026,385 A     6/1991  Schutte et al.
(Continued)

FOREIGN PATENT DOCUMENTS

CN    204318858 U    5/2015
WO    2008/036951 A2  3/2008
(Continued)

OTHER PUBLICATIONS

International Search Report and Written Opinion of the ISA for PCT/EP2019/066899, mailed Aug. 22, 2019, 16 pages.

*Primary Examiner* — Kathleen S Holwerda
*Assistant Examiner* — Serenity A Miller
(74) *Attorney, Agent, or Firm* — NIXON & VANDERHYE (57) ABSTRACT

Surgical knives are disclosed, for initiating percutaneous access to a surgical site. The knife has a body with a rear handle and a front cutter portion. It may have a central cannulation to receive a guide wire, along a front-to-rear operating axis. The cutter portion has first and second blades opposed across the axis, each having an outward cutting edge directed laterally outwardly relative to the operating axis and a flat outward face also directed laterally outwardly relative to the operating axis and transversely to the respective outward cutting edge. The first and second outward faces of the two blades converge forwardly to their tip points, which lie close to the axis, and their cutting edges are oppositely directed. Alternatively a single blade may be used, forwardly convergent with the axis.

21 Claims, 5 Drawing Sheets (51) Int. Cl.
*A61B 17/3209* (2006.01)
*A61B 17/17* (2006.01)

(58) Field of Classification Search
USPC .......................... 30/299, 304; 606/167, 170
See application file for complete search history.

(56) References Cited

U.S. PATENT DOCUMENTS

| | | |
|---|---|---|
| 5,100,391 A | 3/1992 | Schutte et al. |
| 5,447,516 A | 9/1995 | Gardner |
| 5,830,225 A | 11/1998 | Detsch |
| 5,843,108 A | 12/1998 | Samuels |
| 6,077,284 A | 6/2000 | Piraka |
| 6,270,501 B1 | 8/2001 | Freiberg et al. |
| 2004/0181246 A1 | 9/2004 | Heppler |
| 2008/0077146 A1 | 3/2008 | Pernsteiner et al. |
| 2009/0062810 A1 | 3/2009 | Sagara |
| 2011/0087258 A1 | 4/2011 | Sluss |
| 2016/0128712 A1 | 5/2016 | Ruggiero, Sr. |

FOREIGN PATENT DOCUMENTS

| | | |
|---|---|---|
| WO | 2009/103951 A2 | 8/2009 |
| WO | 2013/172998 A2 | 11/2013 |
| WO | 2014/027268 A1 | 2/2014 |
| WO | 2017/133967 | 8/2017 |

SECTION A-A
FIG. 9

SURGICAL INSTRUMENTS

This application is the U.S. national phase of International Application No. PCT/EP2019/066899 filed 25 Jun. 2019, which designated the U.S. and claims priority to GB Patent Application No. 1810403.4 filed 25 Jun. 2018, and GB Patent Application No. 1903277.0 filed 11 Mar. 2019, the entire contents of each of which are hereby incorporated by reference.

BACKGROUND OF THE INVENTION

Field of the Invention

This invention relates to cutting instruments, generally of the fixed-blade type such as knives. Particular practical embodiments of the invention include surgical instruments in the form of surgical knives such as scalpels and plunge knives, especially those for use in initiating percutaneous access to a surgical site. However the concepts described may find use for cutting instruments in other fields.

Description of the Related Art

One particular area of use for the present proposals is percutaneous surgery. Particular examples of this are where a primary movement of surgical instruments, implants or devices relative to a surgical site is in or along a single direction. This may be e.g. laparoscopic surgery. Another illustrative example is a procedure of intramedullary nailing of a long bone such as the femur, humerus or tibia. A rod must be introduced into the hollow, central medullary canal of the bone from its end, typically in the treatment of a fracture or deformity. The appropriate entry point for the nail must be accurately defined and located, and conventionally this has been done by open surgery involving a long incision in the region of the end of the bone followed by open dissection down onto it so that the site can be visually confirmed and the appropriate entry opened up. A similar initial procedure applies for removing a nail.

More recently it has become preferred to insert a sharpened guide wire (in fact a thin rod with substantial rigidity) through the skin and underlying tissue and into the appropriate entry point. This reduces surgical trauma and scarring. The skin and underlying tissue must be divided with a scalpel to form a space for subsequent passage of other instruments. The cutting with a scalpel is usually done freehand around the guide wire, which is a slow and difficult step if inaccuracy or major scarring is to be avoided: the guide wire marks the location but is no help to the cutting itself. Another relevant area is the insertion and removal of orthopaedic screws. Increasingly such screws are inserted and removed percutaneously through a small incision. They may be cannulated screws moved through the incision along a guide wire. The formation of a small "stab" incision for such purposes is a relevant area for the present technology.

There are prior proposals of cannulated scalpels for guided cutting. U.S. Pat. No. 6,270,501B describes a cannulated scalpel with a tubular shaft adapted to slide over a guide wire, with a head having opposed cutting blades projecting to either side in an axial plane, and having leading cutting edges to cut through tissue and narrow trailing edges to facilitate withdrawal. WO2017/133967 describes an instrument similar to that of U.S. Pat. No. 6,270,501B in which the coplanar double blades are detachable from a handle portion. US2011/0087258 is another document describing a cannulated surgical knife.

SUMMARY OF THE INVENTION

The present invention aims to provide new and useful cutting instruments, such as surgical instruments or scalpels, adapted to make an open incision accurately and conveniently, and preferably able to be guided by a guide wire. In surgical uses, desirable features are that operating time and surgical trauma can be reduced or minimized in making an incision and providing satisfactory access to a surgical site, especially in the context of surgery carried out percutaneously.

Aspects of the invention are set out in the claims.

A first aspect of the invention is a surgical instrument, such as a surgical knife or scalpel for providing percutaneous access to a surgical site, and comprising a body and a cutter portion.

The body comprises a handle portion, and is preferably cannulated, the cannulation being to receive a guide wire for guided movement of the instrument in use, and the direction of the cannulation defining an operating axis of the instrument which has a front end and a rear end. If the instrument is not cannulated the front and rear end still define an operating axis direction.

The cutter portion is at the front end of the instrument. In a first aspect the cutter portion comprises first and second blade portions opposed across the operating axis at opposite sides thereof, each of the first and second blade portions having a tip portion at the front end, an outward cutting edge directed laterally outwardly relative to the operating axis, and an outward face also directed laterally outwardly relative to the operating axis and transversely to the respective outward cutting edge. The first and second outward faces of the two blade portions converge with one another forwardly towards their tip portions. Also, first and second cutting edges (that is to say respective outwardly-directed cutting edges of the first and second blade portions) are generally oppositely outwardly directed.

Preferably the tip portions of the first and second blade portions are the parts thereof that lie closest to the operating axis and closest to one another. Additionally or alternatively, the tip portions are disposed so that a line between them at the closest approach of the first and second blade portions passes through the operating axis.

Preferably the tip portions have front points; the above statements about the tip portions are applicable to the front points.

The angle of forward convergence of the outward faces of the first and second blade portions is preferably at least 2°, more preferably at least 4°, still more preferably at least 5°. Conversely it is usually not more than 20° or not more than 15° and preferably not more than 10°. This angle can be regarded as the included angle between the blades' outward faces. It may be the included angle in a plane containing the operating axis. Additionally or alternatively it may be the minimum or maximum included angle that they attain, in any direction (e.g. if they are not both flat).

The outward faces of the first and second blade portions may diverge rearwardly such that the width between them across the operating axis at a rear extremity of the blade portions is at least as wide as the body of the instrument at/or immediately behind that axial position. This can avoid an obstructive step for either direction of cutting movement along the operating axis direction.

The body may have a step formation—an inward step in the forward direction—positioned adjacent a rear end of the blade portion, especially in the case that the blade portion is a discrete attached component, so that the blade rear end is recessed relative to the adjacent body surface rearwardly of it. This can help to reduce or avoid catching of the rear end of the blade portion on withdrawal of the instrument.

The skilled person will understand that the convergent disposition of the first and second blade portions to either side of the operating axis—which in a cannulated embodiment is the locus of the guide wire—enables effectively a single incision/cut to be made by advancing the instrument into the substrate to be cut in the forward direction, that is, forward along the operating axis. The cut can be extended laterally up to a controlled width to either side of the guide wire by means of the oppositely-directed outward edges of the blade portions, which enlarge or lengthen the cut in a cut direction, and can also be opened up in a transverse direction—a separation direction, since the opening corresponds to gaping of the opening rather than extension of the cut line—by the divergence of the blade portions' outward surfaces as the cutter portion penetrates deeper. Desirably the form of the instrument's body is such that the body/handle of the knife does not catch on material (such as skin/tissue) around the cut and obstruct either the cutting movement or a subsequent withdrawal.

Preferably the outward blade faces are flat. This enables the use of readily-available or readily-manufacturable blade elements, which may be standard scalpel blades attached to opposite sides of the body. The blade portions may be discrete blade elements and may be fixed against locating formations of the body including forwardly-convergent locating faces against which the blade elements are held to support them in the desired convergent orientations. The locating formations may include securing formations by which the blade elements are held in place, either removably or permanently. In one preferred embodiment, blade elements constituting the respective blade portions have openings, and retaining formations of the body extend through the openings to hold the blade elements. The retaining formations may be heat-formed or moulded-on so that the blade elements cannot be removed. This would be suitable e.g. for a single-use type instrument. Alternatively the blades may be over-moulded, or bonded onto the body.

The body is typically elongate in form. The body may be a metal unit or of plastics material, for example a one-piece plastics moulding. The handle portion may comprise a laterally- or radially-enlarged grip portion spaced back from the front end, e.g. at or adjacent the rear end. The body may comprise the grip or handle portion, an elongate shaft portion extending in the direction of the operating axis and a blade support portion comprised in the cutter portion of the instrument at the front end.

The preferred cannulation for a guide wire is typically a straight channel, and may extend right through the body from the front end to the rear end thereof. It may have an internal size, typically a circular diameter, of e.g. 1 to 5 mm, more usually 2 to 4 mm. The cannulation is not necessarily fully enclosed by solid material provided that it defines a path that effectively locates and aligns a guide wire relative to the body in use. While a range of cannulation sizes can be provided according to the expected guide wire diameter this is not always necessary; a smaller wire in a larger channel can still give adequate guiding so that e.g. a cannulation between 3 and 3.5 mm in diameter will serve for a wide range of surgical uses.

The first and second blade portions may be similarly convergently angled with respect to the operating axis. Indeed the first and second blade portions in general may be arranged with symmetry, and especially two-fold rotational symmetry, around the operating axis.

The outward cutting edge of one or both of the blade portions may have various forms—straight, concave or convex—but is preferably convex in form. This outward cutting edge preferably extends at least from the tip portion of the blade portion to the part of maximum lateral projection thereof. Preferably the blade portion outward edge extends rearwardly beyond this position of maximum lateral projection, to a rearward region thereof. It may or may not be a (sharpened) cutting edge at this rearward region. This region may also progressively reduce the lateral projection in the rearward direction, i.e. so that the blade portion narrows rearwardly away from the front end. This form helps to ensure that the knife is not only easily inserted into the incision, but also easily withdrawn from it. It is preferred that rearwardly-convergent or rearwardly-directed edges of the blade portions are—partially or wholly—non-cutting edges, since they are not needed for cutting and risk of cutting the user's fingers is then reduced. The extent of the outward cutting edges in the cut direction away from the operating axis, and the divergent angle between them back from the tip in the cutting plane (defined below), together determine the maximum available width of the cut in the cut direction and the rate of increase of the cut width per given length of blade inserted. Blade types and sizes can be selected accordingly. Preferably the initial divergence angle between the cutting edges—initial in the sense of extending back immediately behind their tips/points from the onset of axial overlap—is at least 70°, more preferably at least 80° or at least 90°, projected onto a median plane between them (cutting plane) in which that angle is maximized: this is usually a plane in the cut direction and containing the operation axis along which the blades are advanced in use. Where one or both edges is convex, the edge divergence angle gradually reduces further back.

The first and second blade portions may have inwardly-directed edges that are cutting edges, or are non-cutting edges. Generally the preference is to form a single combined incision extending out in two directions from the operating axis, rather than two separate cuts, so that inward cutting edges of the blade portion may have no significant function and non-cutting edges are then preferred. Indeed, while desirably the first and second blade portions' outward surfaces overlap to some extent (i.e. viewed across the operating axis transversely to the directions of their cutting edges, in the separating direction, so that they are mutually opposed) the overlap need not be great provided that the outward surfaces are sufficient in extent to separate smoothly the opposite sides of the incision and guide them around the body of the instrument. Such oppositely-directed convergent outward surfaces may indeed be constituted partly by structures integral with the body, and not necessarily entirely by blade element faces.

The body may be laterally wider in the separation direction than in the cut direction, e.g. to achieve and maintain greater cut separation. Or, the body or at least a handle portion thereof may be laterally wider in the cut direction than in the separation direction, e.g. to provide a flatter configuration and reduce packaging volume. The body may have an extended or elongate shaft portion which is narrower than the outward extent of the first and second cutting edges, so as easily to be accommodated within the cut opening to an extended depth on further insertion of the instrument into an incision. Optionally in the perpendicular (separation) direction a relatively larger width of the body can hold the incision open.

The tip portions of the blade portions desirably approach closely or intersect a notional forward projection of the operating axis or cannulation opening at the front end of the instrument, so that in use they contact or nearly contact the guide wire. For example, they may each be spaced from the forward projection of the operating axis or cannulation opening by not more than 0.5 mm each, and/or spaced from one another by not more than 3 mm, or by not more than 2 mm or by not more than 1 mm especially where no guide wire is to be used.

Indeed it is preferred to maintain an inward inclination of the blade tips/points in use. It is preferred to minimize the extent to which elements of material or tissue being cut can get in between or inside the blades, possibly causing splaying thereof and/or compromising neatness of cut. It is preferred that the tips of the blades substantially contact the guide wire between them in use, and if there is no guide wire to be used—and perhaps the body is not cannulated for a guide wire—the tips desirably contact or nearly contact one another. The length and form of the blades may be selected accordingly and, if they are discrete blades mounted on the body, the mounting formations appropriately positioned to achieve this. In some embodiments the blade tips may contact one another in the free state (i.e. with no guide wire present). If and when a guide wire is inserted—the size of the wire not being critical—the blade tips can flex slightly away to allow the wire to pass while maintaining a desirably close sliding contact with it.

The tip portions may be diametrically opposed across the operating axis (or a guide wire when in use) in a direction substantially perpendicular to the cut direction, e.g. at at least 60°, or at least 70°, or at least 80°, to that direction.

The convergence of the first and second blade portions stabilises them during the cut, so that they do not tend to separate or wander. It also helps to protect the user's fingers against cutting, and contributes to the formation of essentially a single cut opening despite two spaced blade portions being employed.

In a second aspect of the invention the cutter portion comprises at least one blade portion, in particular a single blade portion, the blade portion having a tip portion at the front end, an outward cutting edge directed laterally outwardly relative to the operating axis, and an outward face also directed laterally outwardly relative to the operating axis and transversely to the outward cutting edge. The outward face of the blade portion converges with the operating axis. In this second aspect, any of the above features as regards the one blade portion's structure and disposition may be as described above for the respective blade portions of the first aspect, except insofar as they specifically relate to the relation of two blade portions as blade portions.

Again, it is particularly preferred:
that the instrument be cannulated for a guide wire along the operating axis;
that a tip (or cutting edge portion adjacent the tip) of the blade portion contacts or closely approaches a notional forward projection of the operating axis or cannulation opening at the front end, so as in use to contact, nearly contact or make interfering contact with a guide wire.

With a single blade portion it is preferred although not essential to use a cutting portion which is double-edged, i.e. has outward cutting edges directed laterally in respective opposite senses of the cut direction. For example such a double-edged cutting portion may be symmetrically shaped as regards the opposite cutting edges. The point or tip thereof may be the closest point to the operating axis (or notional prolongation of a guide wire cannulation).

The angle made by the outward blade face to the operating axis may be as in the first aspect, e.g. at least 1°, more preferably at least 2°, still more preferably at least 2.5°. Conversely it is usually not more than 10° or not more than 7.5° and preferably not more than 5°. The outward blade face is desirably flat.

In this second aspect it is preferred that the body has an outward separation face axially overlapping with at least part of the blade portion and directed oppositely outwardly, the body's separation face converging with the outward face of the blade portion. The convergence angle of the body's separation face may or may not be the same as that of the blade portion. Thus, the angular relation of the body's separation face and the blade portion's outward face may be in accordance with options described above for the respective outward faces of the first and second blade portions of the first aspect. The body's separation face can act in a manner similar to the outward face of the additional blade portion in the first aspect, acting to open up an incision being made by the cutting action of the blade portion. It may be straight in cross-section, i.e. converge at a substantially constant angle, and it may be flat. Or, a portion of the body's separation face may have those properties. The body's separation face would of course not reach axially as far forward as the tip of the blade portion, since it is not a cutter, but desirably there is at least 30% or at least 50% or at least 70% axial length overlap of the convergent separation face with the whole of the blade portion.

The single-bladed option has an advantage of economy and simplicity, in combination with effects as listed above for the first aspect.

In embodiments which are a surgical instrument such as a scalpel or plunge knife, a preferred optional feature is a conduit incorporated in the surgical instrument for feeding a fluid to the front end thereof during use, especially a liquid, which may be a therapeutic substance or medicament, an anaesthetic, vasoconstrictor or any combination of these. In particular, the availability of anaesthetic and/or vasoconstriction action at the cutting location may substantially reduce the time taken to create the incision. The conduit may be a discrete tube, the body of the instrument defining a channel or grip to hold the end portion of the discrete tube so that fluid from it is directed or fed to the front end, e.g. through an inlet leading into a cannulation that takes a guide wire, or to a point substantially coincident with a front opening of such a cannulation.

In a surgical context it is envisaged that the ability of such a surgical instrument to open up an incision progressively, in a direction transverse to the cut direction, may conveniently be exploited to facilitate the insertion of further devices or instruments at the opened site. For example a tubular member e.g. in the form of a sheath may be fitted over the body of the cutting instrument (surgical instrument) behind the blade portions, either before or after its use to form the incision, and then advanced into the incision either with the instrument or subsequently, after which the instrument can be withdrawn through the tubular element leaving the latter in place in the incision. The tubular element might for example constitute a protective channel through which a further surgical procedure such as cutting bone could be done, protecting the surrounding tissue from damage by drills, reamers and the like.

It is envisaged that a surgical cutting instrument as proposed may be used in or adapted for a variety of surgical indication where percutaneous surgery is to be done. In addition to the intramedullary nailing of bones as described, such surgical knives may find use in the fixation of bones or ligaments, the fitting or replacing of percutaneous screws, the percutaneous removal of devices from bone—including nails, pins, implants and other items—and use in the percutaneous fusion of joints.

BRIEF DESCRIPTION OF THE DRAWINGS

Embodiments of the invention are now described by way of example, with reference to the accompanying drawings in which.

DESCRIPTION OF THE PREFERRED EMBODIMENTS

Figure 1:
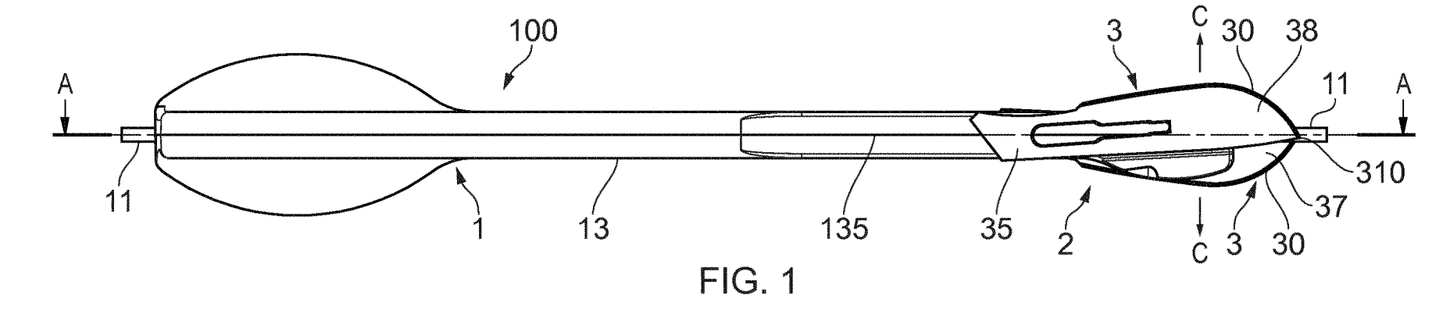
FIG. 1 is a side view of a surgical instrument which is a first embodiment of the invention, in the nature of a scalpel or plunge knife, showing also a guide wire.

Referring firstly to FIG. 1, a surgical instrument embodying our proposals is shown in the form of a scalpel or plunge knife 100. It consists essentially of a straight elongate body 1 with a handle or grip portion 12 at its rear end, a central shaft portion 13 and a cutter portion 2 at its front end. The cutter portion consists of a blade mounting portion 5 of the body 1 and a pair of blades 3. In this embodiment the body is formed of injection-moulded plastics material and the blades are steel scalpel blades.

The body is penetrated by a longitudinal central cannulation 14, being a straight cylindrical passage extending through the instrument and providing for it to be mounted on a metal guide wire 11 (only a short segment of the guide wire being shown) so that the instrument can be slid along the guide wire 11 in use. As is well known, guide wires are used to guide the direction, position and orientation of a surgical instrument in relation to a selected surgical site.

At the cutter portion 2, a pair of identical steel scalpel blades 3—constituting the blade portions of the concept described above—are mounted opposed across the axis defined by the central cannulation 14 and guide wire 11. Each blade 3 has a cutting edge 3 directed generally laterally outwardly relative to the axis and leading forward to a point 310 adjacent the axis, lying closely against the guide wire 11 in use (see FIG. 2).

Figures 2, 3, 4:
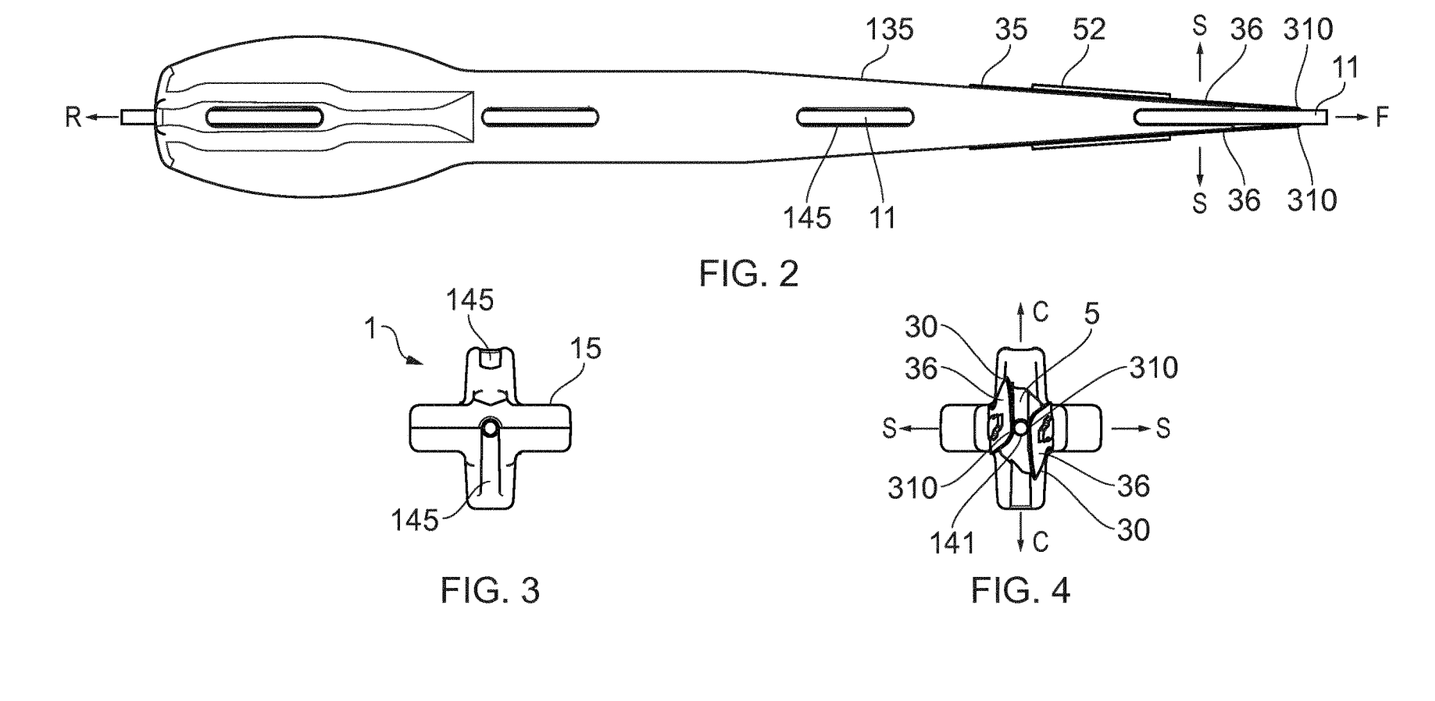
FIG. 2 is a further side view of the first embodiment taken at 90° to the FIG. 1 view.
FIG. 3 is an end view from the rear end.
FIG. 4 is an end view from the front end.

The following terminology is used to refer to the orientation of the various components. A forward direction (F) and a rearward direction (R) are defined longitudinally as indicated in FIG. 2. Then, with reference to the front end view of FIG. 4, it can be seen that laterally the outward faces 36 of the respective blades 3 are directed oppositely away from each other, and these outward lateral directions are designated the separation direction (S). The curved cutting edges 30 of the blades are directed in respective lateral directions opposite and approximately parallel to one another and also perpendicular to the separation direction S, and these directions are designated the cut direction C. Immediately behind the points, tangents to the cutting edges initially diverge from one another (in the cut direction) at about 110°.

With reference to the use of the instrument, it will be understood that the instrument is advanced forwardly into the skin and underlying tissue along the guide wire 11, entering at the points 310 of the two blades 3 and thereafter enlarging a cut simultaneously in opposite directions in the cut direction C, while opening up or spreading the sides or walls of the cut away from each other in the separation direction S. This separation is achieved by the advancing of the instrument in combination with the rearward divergence of the outward surfaces 36 of the blades 3, continuing with a correspondingly divergent region 135 of the body shaft 13 behind the blades. The divergent outward surfaces progressively separate and open the sides of the incision.

While the separation and cut directions are proposed as orthogonal directions radial of the axis defined by the central cannulation 14 (the operating axis in this embodiment), references to components or motions being directed in the separation direction, cut direction or axial direction are not necessarily intended to require exact alignment with those directions, but general alignment with those directions for functional purposes. They are terms for ease of explanation and description.

The grip portion 12 has a set of radial grip projections 15—here in the form of lobes but they could take a variety of forms—so that the user can easily control the direction and rotational alignment of the instrument. The central cannulation 14 is open laterally through a series of windows 145 opening alternately to opposite sides of the body 1. These are not functional in the instrument, but are to facilitate moulding of a component having the desired cannulation. The method uses plural radially-inserted mould elements, at a series of respective adjacent longitudinal regions which are axially adjoining but circumferentially spaced. It enables formation of a long central bore, effectively of uniform diameter (since the narrow side openings do not allow escape of a stiff wire), without the need for a removable longitudinal mandrel (which would require a draft angle and give non-uniform diameter), or a separate boring or drilling step. This method may be an independent aspect of our proposals.

Figure 5:
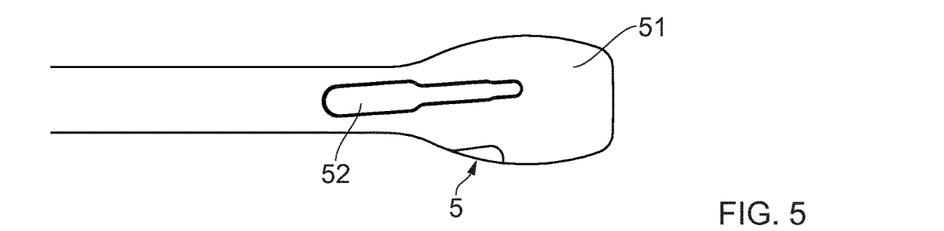
FIG. 5 is an enlarged side view of the front end of the body with the blades removed, showing a blade mounting portion from the same direction as in FIG. 1.
Figure 6:
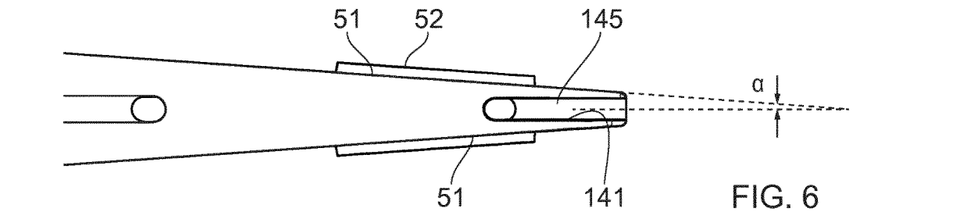
FIG. 6 is a view of the blade mounting portion from the same direction as in FIG. 2.
Figure 7:
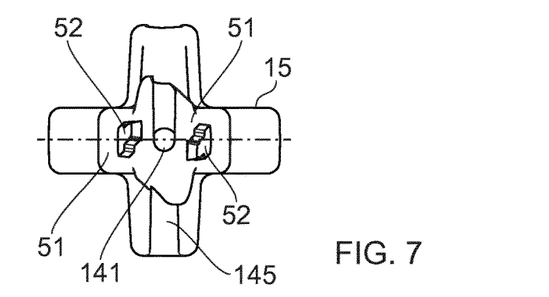
FIG. 7 is a view of the body with the blades removed from the front end.

At the front end of the body 1 the blade mounting portion 5 (see also FIGS. 5-7) has a generally spatulate form with a pair of opposed flat blade support surfaces 51 which are angled towards each other at a convergence angle of 8°, and are angled symmetrically to either side of the operating axis. That is to say, the (minimum) angle α—see FIG. 6—between each support surface 51 and the operating axis is 4°. The front opening 141 of the central cannulation 14 is at their front ends. A shaped stake projection 52 in the form of an elongate rib projects up from each blade support surface 51 and fits a correspondingly-shaped mounting slot 38 of the blade 3 so as to assure its exact longitudinal orientation. The blade 3 can be fixed in place by conventional "staking" i.e. heat-deforming the stake elements 52 so that they spread down over the outer surfaces of the blades; this is a well-known technique.

Figure 8:
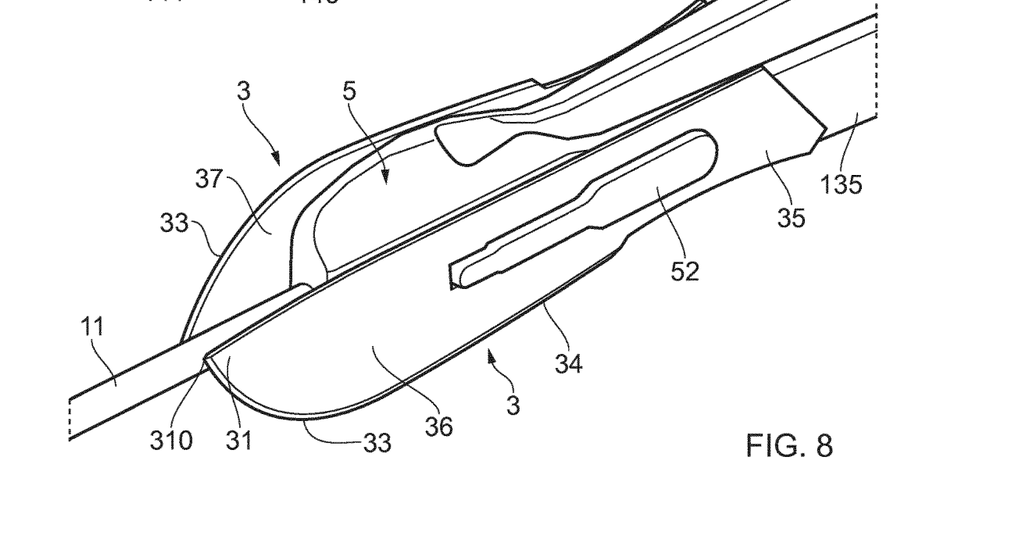
FIG. 8 is an enlarged oblique view of the front end of the instrument on a guide wire.
Figure 9:
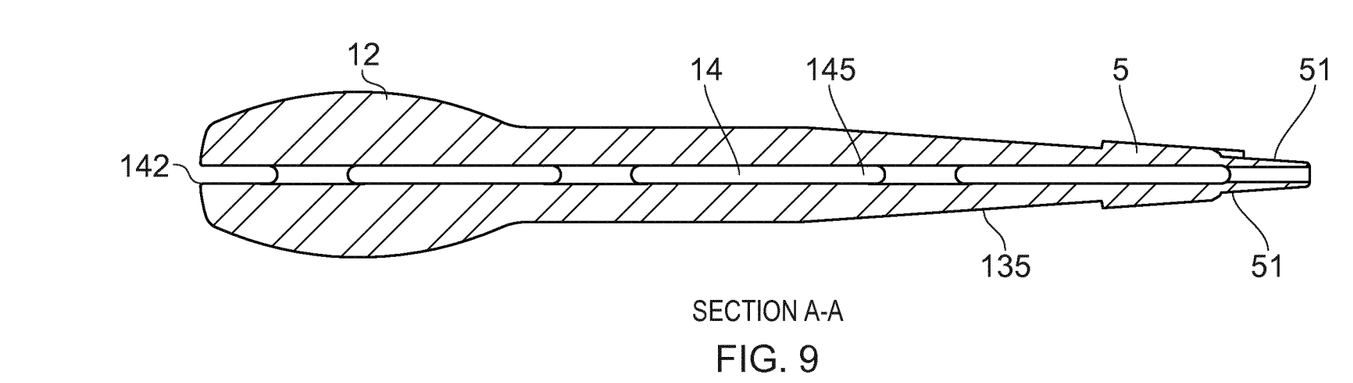
FIG. 9 is a section through the body at A-A of FIG. 1.
Figure 10:
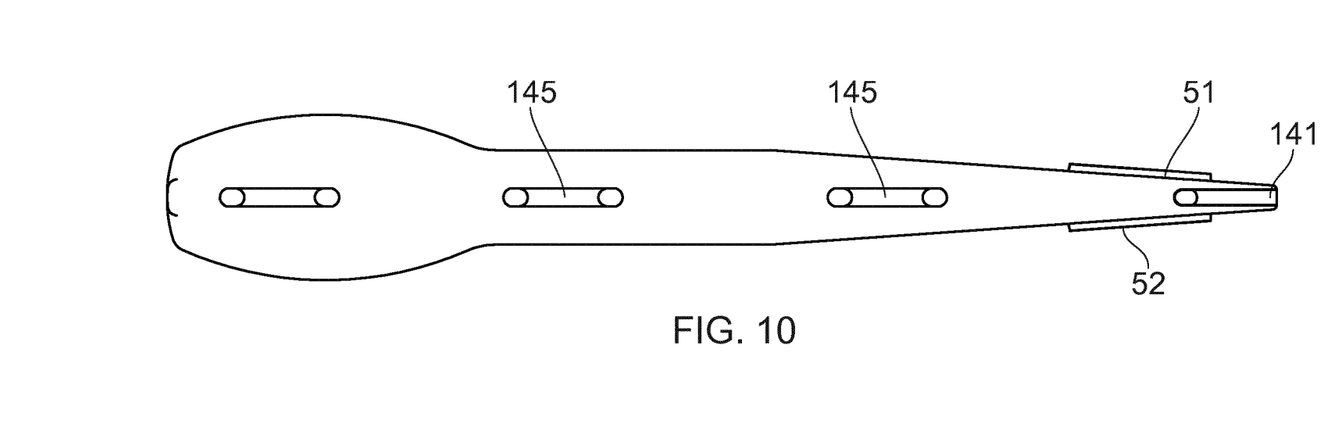
FIG. 10 is a side view of the body from the same direction as FIG. 2, with the guide wire and blades absent.

In the fitted position—see also FIG. 8—the tip regions 31 of the blades project forwardly of the front end of the body so that the extreme points 310 of the blades touch the guide wire 11 emerging between them. In this embodiment the blades are mounted so that when the guide wire is absent their points nearly touch, and are therefore positively urged against the guide wire surface with a slight bias owing to resilient flexion of the blades as the guide wire is inserted. This helps to avoid cut tissue catching between or behind the blade tips. The blades in this embodiment are single-edged, with a relatively straight non-cutting and non-functional rear edge 38 which extends down to the point 310, and a convex cutting edge 30 extending from the tip 310 around the convex belly 33 of the blade reaching the maximum lateral projection from the axis, and then a trailing or rearward region 34 descending back towards the non-sharpened shank 35 at the rear end of the blade, which is functional only for location and handling. The blades are flat, and identical to one another. Such scalpel blades are readily commercially available: the ones shown are of the No. 22 pattern and a variety of similar forms are available, such as numbers 10, 13, 18, 19, 20-24 and 36. However it is desirable that the blade presents a substantial planar and plain outward face, for which purpose blade types 22, 22a and 24 are especially suitable. However depending on the application, blades of substantially different forms may be used. They need not necessarily have convex cutting edges. Equally they need not be single-edged, they might be double edged with cutting edges directed in both directions relative to the axis although this may be redundant if the two blade portions co-operate to form a single incision which is the preferred action. Also it is possible that the outward face of one or both of the blade portions is not planar but convex, e.g. convexly curved, in a section plane transverse to the operating axis.

Figure 11:
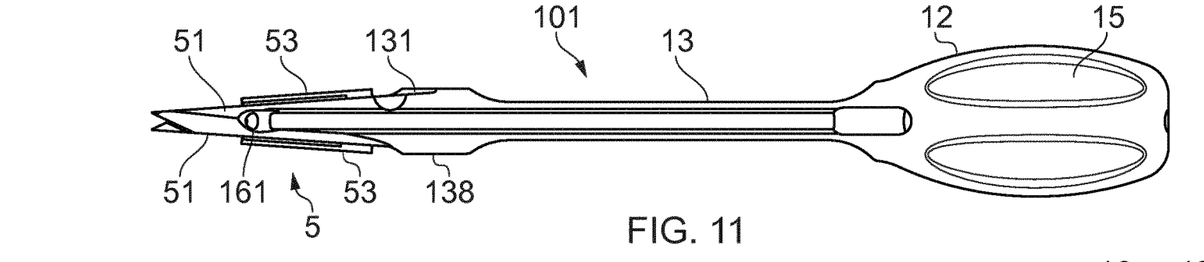
FIG. 11 is a side view of the body of a second embodiment of surgical instrument of the same general type as the first embodiment.
Figure 12:
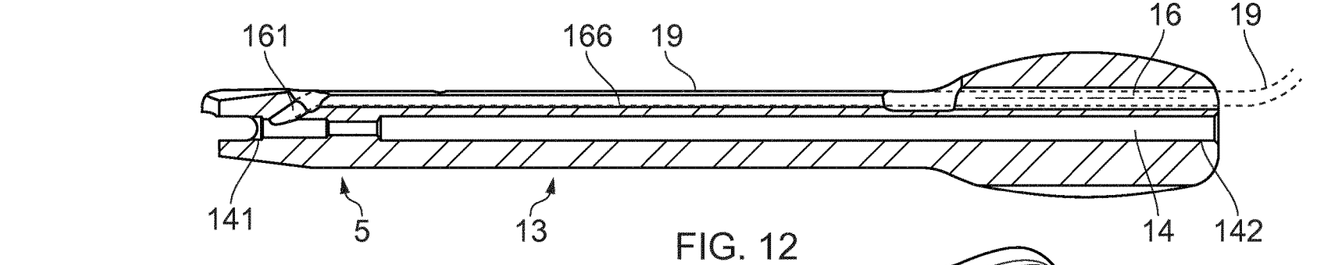
FIG. 12 is a longitudinal cross-sectional view of the body of the second embodiment.
Figure 13:
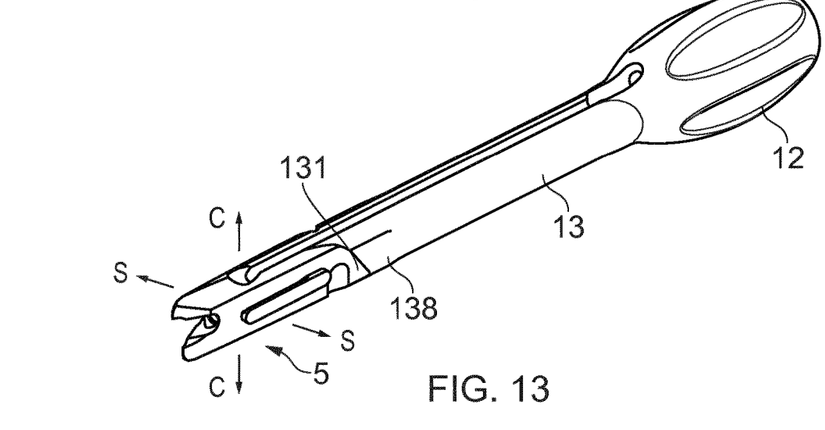
FIG. 13 is an oblique view of the surgical instrument body of the second embodiment.

FIGS. 11 to 13 show the body of a second embodiment having the same general features as the first embodiment, so that the corresponding reference numerals are used. A first difference is that the body 1 is of stainless steel rather than injection-moulded plastics. As a result the cannulation 14 can be a simple drilled bore and the shaft portion 13 is rather more slender especially in the separation direction. This embodiment has a local lateral enlargement or shoulder 138 of the body just behind the rear ends of the blades (blades not shown) to maintain separation of the sides of the incision in front of the narrower shaft portion. The mounting ribs 52 are formed with overhangs to trap the blades in position. The convergent angle of the blade support surfaces 51 and the types of blades to be used may be the same as for the first embodiment.

A further feature shown here is the provision of a supplementary channel 16 running alongside the cannulation 14 and acting as a locating holder for a conduit such as a flexible medication tube 19 (shown in broken lines in FIG. 12) for feeding liquid medication such as a local anaesthetic and/or a vasoconstrictor such as adrenaline to the cutting site. The front end of the channel 16 angles in through the body at a front feed inlet portion 161 to intersect the cannulation 14 so that liquid medication can be fed out through the front opening 141 thereof at the time of making the incision.

Figure 14:
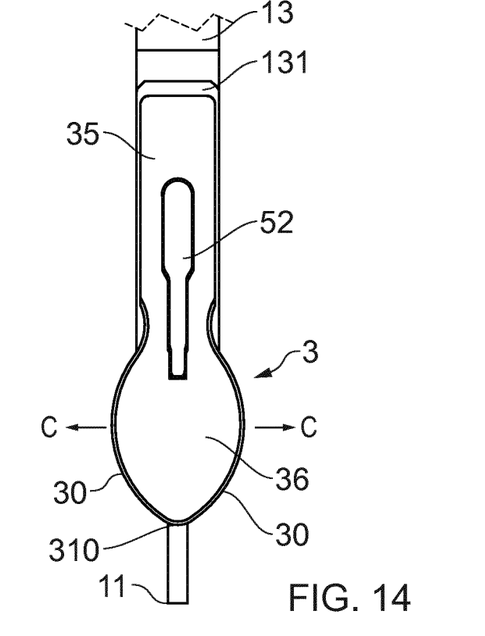
FIG. 14 is a fragmentary side view of the front end of a third embodiment of the invention, being a single-bladed scalpel or plunge knife, showing also a guide wire.
Figure 15:
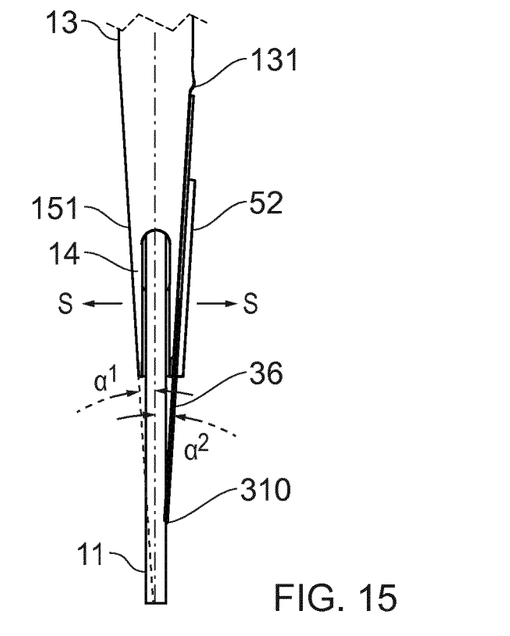
FIG. 15 is a further side view of the third embodiment taken at 90° to the FIG. 14 view.

FIGS. 14 and 15 show the front end of a third embodiment, with a single blade. The body and its handle may be as in previous embodiments. Reference numerals refer to the same parts as above.

The cutter portion consists of a single steel scalpel blade 3 which is flat, and has an inward surface lying against an outward support face of the body's blade support portion defining a predetermined angle with the operating axis as in the embodiments above. In this case the angle ($\alpha^2$ in FIG. 15) is 3.5°. Blade 3 is double-edged and symmetrical in its plane about its longitudinal centre line. It has a central tip 310 positioned so as to be closely in contact with the guide wire 11 in use as shown in FIG. 15 (optionally with some slight interference). The cutting edge 30 continues up divergently to either side of the tip 310 as a pair of convex laterally-directed cutting edges each directed in a respective sense of the cut direction C. Reaching a maximum lateral dimension, the convex cutting edges then converge back upwardly and inwardly to a neck where they meet a shank portion 35 for anchoring of the blade 3 to the support surface of the body shank 13. The shank portion does not have cutting edges. As in the second embodiment above, the body surface makes a shallow step 131 immediately behind the rear edge of the blade 3. The rear edge is recessed in front of the step so as not to catch on withdrawal of the instrument.

On the side opposite from the single blade the body's blade support portion has a plain smooth surface 151 acting as a separation surface, in the sense that it is smoothly convergent in the forward direction towards the operating axis. As the scalpel or plunge knife is inserted into an incision made by the blade 3, it acts in concert with the opposed outward face 36 of the blade 3 to open up the incision. In this embodiment the body's separation face 151 includes a flat surface which makes a convergence angle ($\alpha^1$ in FIG. 15) the same as that of the blade surface i.e. 3.5°, but of course in practice it might not be the same.

In this embodiment the opposed separation surface 151 of the body terminates about half-way along the blade 3 (the blade length considered as a whole, since its entire outward surface including the shank can act for guiding the opening of an incision). In alternative embodiments the opposed body portion might continue forwardly of this, and may be shaped to approach more closely to the blade tip around the cannulation opening (assuming that a cannulation is provided). This single-blade embodiment has the advantage of simplicity and economy since only one blade is required.

Figure 16:
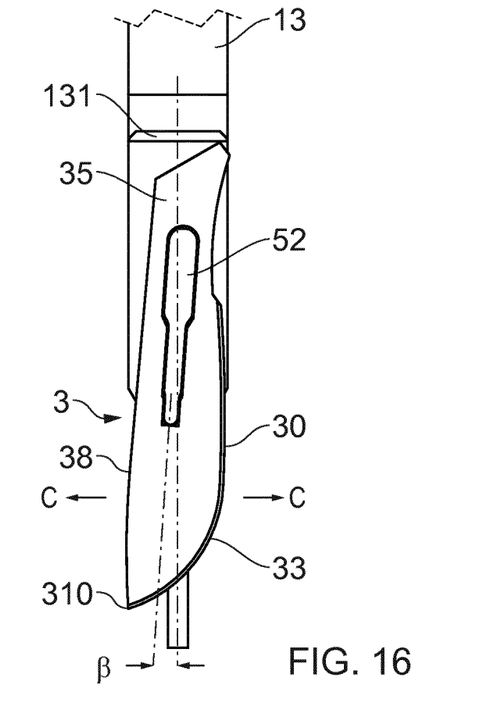
FIG. 16 is a fragmentary side view of the front end of a fourth embodiment of the invention, being a single-bladed scalpel or plunge knife, again showing also a guide wire.
Figure 17:
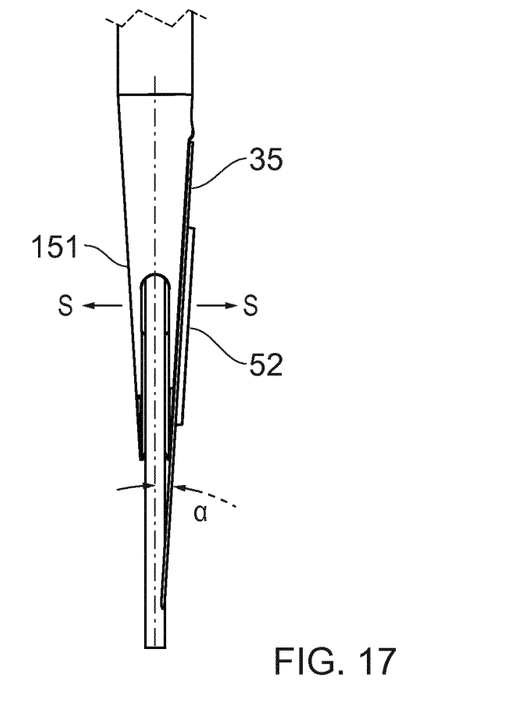
FIG. 17 is a further side view of the fourth embodiment taken at 90° to the FIG. 16 view.

The illustrated blade in the third embodiment is not a standard scalpel blade. FIGS. 16 and 17 show a fourth embodiment, in the same views as for the third embodiment, illustrating as an alternative the use of a standard single-edged scalpel blade—here a No. 22 blade as in the first and second embodiments—with the same body form and angling of the blade surface as in the third embodiment. A difference here is that the blade is slightly tilted across the axis so that, viewed in the separation direction as in FIG. 16, the operating axis falls about half-way (laterally) across its cutting edge. For the illustrated No. 22 blade this is an inclination β to the axis (FIG. 16) of about 4° for the standard mounting slot (as projected onto a plane containing the operating axis that makes the smallest angle with the blade plane). This disposes the cutting edge 30 so that the incision will be formed to either side of the cannulation line to a similar lateral extent.

The closest approach of the blade edge 30 to the guide wire 11 is desirably a contacting approach. Since the tip point 310 of this blade form extends axially in front of that contact point, and also represents the furthest lateral extent on that side, the tip point 310 projects slightly inwardly—as viewed in the cut direction C, FIG. 17—to overlap the locus of the guide wire in use.

Operation in practice is the same as for the previous embodiments. The tip point 310 can initiate an incision effectively although it does not lie closest to the operating axis.

NOTES

In respect of numerical ranges disclosed in the present description it will of course be understood that in the normal way the technical criterion for the upper limit is different from the technical criterion for the lower limit, i.e. the upper and lower limits are intrinsically distinct proposals.

For the avoidance of doubt it is confirmed that in the general description above, in the usual way the proposal of general preferences and options in respect of different features of the surgical instrument constitutes the proposal of general combinations of those general preferences and options for the different features, insofar as they are combinable and compatible and are put forward in the same context.

The invention claimed is:

1. A surgical instrument that is a surgical knife configured to provide percutaneous access to a surgical site, the surgical instrument comprising:
   a rear end;
   a front end;
   an operating axis extending from the rear end to the front end;
   a cutter portion at the front end, the cutter portion comprising first and second blade portions opposed across the operating axis at opposite sides thereof, each of the first and second blade portions having
      a tip portion at the front end,
      an outward cutting edge directed laterally outwardly relative to the operating axis, and
      an outward face directed laterally outwardly relative to the operating axis and transversely to the respective outward cutting edge, the outward faces of the respective two blade portions converging with one another forwardly towards the tip portions thereof, respective said outward cutting edges of the first and second blade portions being generally oppositely outwardly directed relative to the operating axis, the tip portions of the first and second blade portions being the parts thereof that lie closest to the operating axis and closest to one another; and
   a body having a handle portion at the rear end.

2. The surgical instrument of claim 1, wherein the body defines a cannulation along the operating axis, to receive a guide wire configured to guide movement of the instrument in use.

3. The surgical instrument of claim 1, wherein said tip portions are points.

4. The surgical instrument of claim 1, wherein the angle of forward convergence of the outward faces of the first and second blade portions is at least 2°, and not more than 20°.

5. The surgical instrument of claim 1, wherein said outward faces of the first and second blade portions are flat.

6. The surgical instrument of claim 1, wherein the outward faces of the first and second blade portions diverge rearwardly such that the width between the first and second blade portions across the operating axis at a rear extremity of the cutter portion is at least as wide as the body of the instrument immediately behind the rear extremity.

7. The surgical instrument of claim 1, wherein the first and second blade portions are respective discrete scalpel blades attached to opposite sides of the body at a blade support portion thereof.

8. The surgical instrument of claim 1, wherein the first and second blade portions are fixed against locating formations of the body including forwardly-convergent locating faces against which the first and second blade portions are held, the locating formations including securing formations by which the first and second blade portions are held in place.

9. The surgical instrument of claim 8, wherein blade elements constituting the respective first and second blade portions have openings, and the securing formations of the body extend through the openings to hold the blade elements.

10. The surgical instrument of claim 1, wherein said outward cutting edge of one or both of the first and second blade portions is convex in form.

11. The surgical instrument of claim 1, wherein
   said outward cutting edge of one or both of the first and second blade portions extends from the tip portion at least to a position of maximum lateral projection thereof,
   the blade portion outward edge continues rearwardly beyond the position of maximum lateral projection to a rearward region, and
   at the rearward region, all or part of the outward edge is not a sharp edge.

12. The surgical instrument of claim 1, wherein the first and second blade portions are arranged with symmetry around the operating axis.

13. The surgical instrument of claim 1, wherein the tip portions of the first and second blade portions are each spaced from the forward projection of the operating axis, or of a cannulation when present, by not more than 0.5 mm, and/or are spaced from one another by not more than 2 mm or by not more than 1 mm.

14. A surgical instrument that is a surgical knife configured to provide percutaneous access to a surgical site, the surgical instrument comprising:
   a rear end;
   a front end;
   an operating axis extending from the rear end to the front end;
   a single blade at the front end, the single blade having
      a tip portion at the front end,
      an outward cutting edge directed laterally outwardly relative to the operating axis, and
      an outward face directed laterally outwardly relative to the operating axis and transversely to the outward cutting edge, the outward face of the single blade converges forwardly with the operating axis; and
   a body having a handle portion at the rear end,
   wherein the front end of the body has an outward separation face axially overlapping with at least part of the single blade and directed outwardly in the opposite direction to the outward face of the single blade, the outward separation face of the body converging forwardly with the outward face of the single blade.

15. The surgical instrument of claim 14, wherein the body defines a cannulation along the operating axis, to receive a guide wire configured to guide movement of the instrument in use.

16. The surgical instrument of claim 14, wherein the tip portion of the single blade is the part thereof that lies closest to the operating axis.

17. The surgical instrument of claim 14, wherein said tip portion is a point.

18. The surgical instrument of claim 14, wherein the single blade is double-edged.

19. The surgical instrument of claim 14, wherein the angle of forward convergence of the outward face of the single blade and the operating axis is at least 1°, and not more than 10°.

20. The surgical instrument of claim 14, wherein said outward face of the single blade is flat.

21. The surgical instrument of claim 1, further comprising a conduit configured to feed a fluid to the front end thereof during use.

* * * * *